(12) United States Patent
Lorenz et al.

(10) Patent No.: US 9,169,185 B2
(45) Date of Patent: Oct. 27, 2015

(54) METHOD FOR THE PREPARATION OF POLYETHER POLYOLS

(75) Inventors: Klaus Lorenz, Dormagen (DE); Joerg Hofmann, Krefeld (DE)

(73) Assignee: Bayer Intellectual Property GmbH, Monheim (DE)

( * ) Notice: Subject to any disclaimer, the term of this patent is extended or adjusted under 35 U.S.C. 154(b) by 92 days.

(21) Appl. No.: 13/994,842

(22) PCT Filed: Dec. 19, 2011

(86) PCT No.: PCT/US2011/073164
§ 371 (c)(1),
(2), (4) Date: Jun. 17, 2013

(87) PCT Pub. No.: WO2012/084762
PCT Pub. Date: Jun. 28, 2012

(65) Prior Publication Data
US 2013/0338331 A1    Dec. 19, 2013

(30) Foreign Application Priority Data
Dec. 20, 2010  (DE) ................ 101 95 882.5

(51) Int. Cl.
| | |
|---|---|
| C08G 18/48 | (2006.01) |
| C08G 65/28 | (2006.01) |
| C08G 65/30 | (2006.01) |
| C07C 41/03 | (2006.01) |
| C07C 41/44 | (2006.01) |
| C07C 43/10 | (2006.01) |
| C07C 43/13 | (2006.01) |
| C07C 43/11 | (2006.01) |
| C08G 18/32 | (2006.01) |
| C07C 41/14 | (2006.01) |
| C07C 41/34 | (2006.01) |
| C07C 41/02 | (2006.01) |
| C08G 65/26 | (2006.01) |
| C08G 101/00 | (2006.01) |

(52) U.S. Cl.
CPC ............. *C07C 41/44* (2013.01); *C07C 41/02* (2013.01); *C07C 41/03* (2013.01); *C07C 41/14* (2013.01); *C07C 41/34* (2013.01); *C07C 43/10* (2013.01); *C07C 43/11* (2013.01); *C07C 43/135* (2013.01); *C08G 18/3203* (2013.01); *C08G 18/48* (2013.01); *C08G 18/4804* (2013.01); *C08G 18/4825* (2013.01); *C08G 18/4833* (2013.01); *C08G 18/4837* (2013.01); *C08G 18/4845* (2013.01); *C08G 18/4866* (2013.01); *C08G 65/2606* (2013.01); *C08G 65/269* (2013.01); *C08G 65/2648* (2013.01); *C08G 65/2651* (2013.01); *C08G 65/2663* (2013.01); *C08G 65/2672* (2013.01); *C08G 65/2696* (2013.01); *C08G 65/30* (2013.01); *C08G 2101/005* (2013.01); *C08G 2101/0008* (2013.01); *C08G 2101/0083* (2013.01)

(58) Field of Classification Search
IPC ........... C07C 41/02, 41/03, 41/34, 41/44, 43/10, C07C 43/135; C08G 18/48, 18/4866, 18/4833, C08G 18/4837, 18/4845, 65/2606, 65/2648, C08G 65/2651, 65/2663, 65/2672, 65/269, C08G 65/2696, 65/30
See application file for complete search history.

(56) References Cited

U.S. PATENT DOCUMENTS

| | | | |
|---|---|---|---|
| 5,470,813 A | 11/1995 | Le-Khac | |
| 6,482,993 B1 | 11/2002 | Hofmann et al. | |
| 6,642,423 B2 | 11/2003 | Clement et al. | |
| 6,833,431 B2 | 12/2004 | Hofmann et al. | |
| 7,008,900 B1 | 3/2006 | Hofmann et al. | |
| 7,811,958 B2 | 10/2010 | Bohres et al. | |
| 8,119,825 B2 | 2/2012 | Triller et al. | |
| 8,501,904 B2 * | 8/2013 | Lorenz et al. | 528/405 |
| 8,865,945 B2 * | 10/2014 | Lorenz et al. | 568/621 |
| 2006/0223979 A1 * | 10/2006 | Ostrowski et al. | 528/425 |

FOREIGN PATENT DOCUMENTS

| | | |
|---|---|---|
| EP | 0090445 | 10/1988 |
| EP | 0700949 B1 | 3/1999 |
| EP | 0743093 B1 | 12/2001 |
| EP | 0761708 B1 | 3/2003 |
| EP | 1577334 B1 | 2/2008 |
| EP | 1400281 B1 | 7/2010 |
| WO | 9729146 | 8/1997 |
| WO | 9740086 | 10/1997 |
| WO | 9803571 | 1/1998 |
| WO | 9816310 | 4/1998 |
| WO | 9914258 | 3/1999 |
| WO | 0153381 A1 | 7/2001 |
| WO | 1528073 A1 | 5/2005 |

* cited by examiner

*Primary Examiner* — Rabon Sergent
(74) *Attorney, Agent, or Firm* — N. Denise Brown

(57) ABSTRACT

The invention relates to methods for the preparation of polyether polyols by DMC-catalysed alkylene oxide addition to starter compounds comprising acidic sulfuric acid salts, to the use thereof for the preparation of polyurethanes, and to polyurethanes comprising the polyether polyols according to the invention.

19 Claims, No Drawings

METHOD FOR THE PREPARATION OF POLYETHER POLYOLS

FIELD OF THE INVENTION

The present invention provides a method without working-up for the preparation of polyether polyols, the polyether polyols obtainable by the method without working-up, and the use of the polyether polyols according to the invention for the preparation of polyurethanes.

BACKGROUND OF THE INVENTION

Polyether polyols which are suitable for the preparation of polyurethanes can be obtained by means of various preparation methods. On one hand, base-catalysed addition of alkylene oxides to H-functional starter compounds, and on the other hand the use of double metal cyanide compounds as catalysts ("DMC catalysts") are of significance for the addition of alkylene oxides to H-functional starter compounds on an industrial scale. The (Lewis) acid-catalysed addition of alkylene oxides to suitable starter compounds is of secondary importance.

Undesirable secondary reactions increase considerably with increasing molar mass of the polymer under alkali metal hydroxide catalysis. In particular, mention should be made here of the isomerisation of propylene oxide to allyl alcohol, which at high equivalent weights (or low hydroxyl values) results in a high proportion of monofunctional polyether species in the reaction mixture. The monofunctional polyether molecules have an adverse effect on the full curing behaviour and the profile of physical properties of polyurethane systems.

The use of DMC catalysts has made it possible to push ahead with the addition of alkylene oxides, in particular propylene oxide, to H-functional starter compounds down to very low hydroxyl values, without the above-mentioned isomerisation of propylene oxide to allyl alcohol occurring to a significant extent. Highly active DMC catalysts, which are described e.g. in U.S. Pat. No. 5,470,813, EP-A 700 949, EP-A 743 093, EP-A 761 708, WO-A 97/40086, WO-A 98/16310 and WO-A 00/47649, in addition have exceptionally high activity and permit polyether polyol preparation at very low catalyst concentrations (25 ppm or less), so that it is no longer necessary to separate off the catalyst from the finished product. Typical examples are the highly active DMC catalysts described in EP-A 700 949, which in addition to a double metal cyanide compound (e.g. zinc hexacyanocobaltate(III)) and an organic complexing ligand (e.g. tert-butanol) also comprise a polyether polyol having a number-average molar mass of greater than 500 g/mol.

One characteristic of DMC catalysts is their pronounced sensitivity to high concentrations of hydroxyl groups, which are caused for example by large amounts of starters such as ethylene glycol, propylene glycol, glycerol, trimethylol propane, sorbitol or sucrose, and polar impurities of the reaction mixture. The DMC catalysts cannot then be converted into the polymerisation-active form during the reaction initiation phase, or alkylene oxide addition reactions which are already running may come to a halt due to the continuous supply of high concentrations of hydroxyl groups and polar impurities. Impurities may for example be water, compounds with a high number of hydroxyl groups which are in close proximity, such as carbohydrates and carbohydrate derivatives, or compounds with basic groups such as for example amines. Substances with carbonyl groups which are in close proximity, or carbonyl groups which are adjacent to hydroxyl groups also have an adverse effect on the catalyst activity. In order nevertheless to be able to subject starters having high concentrations of OH groups, or starters having impurities which are to be regarded as catalyst poisons to DMC-catalysed alkylene oxide addition reactions, the hydroxyl group concentration has to be lowered or the catalyst poisons rendered harmless, respectively. For this purpose, first prepolymers can be prepared from these starter compounds by means of base catalysis, which prepolymers then after working-up are converted into the desired alkylene oxide addition products of high molar mass by means of DMC catalysis. What is disadvantageous with this procedure is that the prepolymer obtained by means of base catalysis has to be worked up very carefully in order to rule out deactivation of the DMC catalyst by basic catalyst traces introduced by the prepolymer.

This disadvantage can be overcome by the method of continuous metering of starter which is disclosed in WO-A 97/29146. In this case, critical starter compounds are not initially introduced into the reactor, but continuously supplied to the reactor during the reaction in addition to the alkylene oxides. Prepolymers can be initially introduced as starting medium for the reaction in this method, and also it is possible to use small amounts of the product to be prepared itself as starting medium. The necessity of first having to prepare prepolymers which are suitable for further alkylene oxide additions separately is thus dispensed with.

Likewise, polyether polyols can be prepared fully continuously without working-up in accordance with a method as described in WO-A 98/03571. In this case, in addition to one or more alkylene oxides and one or more starters, the DMC catalyst is also supplied continuously to the reactor or to a reactor system under alkoxylation conditions, and the product is removed continuously from the reactor or the reactor system after a pre-selectable average residence time.

Both the method of continuous starter admetering and the fully continuous polyether polyol preparation method have the disadvantage that polyethers with block structures, in particular those with short internal blocks, can be prepared only with great difficulty: in the case of the method of continuous starter admetering, the admetering of starter has to be concluded already before the end of the metering of the first alkylene oxide block in order to obtain products with homogeneously distributed block lengths. This is difficult in particular when internal blocks with block equivalent molar masses of 53 Da to 350 Da are desired, since it then becomes necessary to increase the ratio of starter to alkylene oxide in the admetered educt stream such that again there is the risk of attaining critical concentrations of hydroxyl groups and polar impurities. In such cases, the catalysts increasingly lose activity during the starter admetering phase, which manifests itself e.g. by an increase in pressure in the reactor as a result of an increasing concentration of free alkylene oxide. In the fully continuous polyether polyol preparation method, costly series of reactors and hold-up sections with a continuous throughflow have to be installed for products with block structures. Both the continuous starter admetering method and the fully continuous method are furthermore only poorly suited for converting high-melting starter compounds or starter compounds which decompose below the melting point, such as for example sugar, sorbitol or pentaerythritol, into long-chain polyols without working-up. Such starters have to be metered via expensively heated metering sections or in solution.

"Equivalent molar mass" is to be understood to mean the total mass of the material comprising active hydrogen atoms divided by the number of active hydrogen atoms. In the case of materials containing hydroxyl groups, it is calculated by the following formula:

equivalent molar mass=56,100/hydroxyl value [mg KOH/g]

The hydroxyl value can be determined e.g. titrimetrically in accordance with the specifications of DIN 53240 or spectroscopically by means of NIR.

EP-A 0 090 445 claims the addition of catalyst "promoters" in order to increase the activity of DMC catalysts of an older generation. Such "promoters" are salts of at least divalent metal cations and metal-free anions, and/or metal-free acids. The "promoters" are added separately to the catalyst/starter mixture. It is emphasised that the absence of alkali metal salts is essential, since these reduce the activity of DMC catalysts. Given this background, the present invention is particularly surprising.

EP-A 1 400 281 claims salt-containing, in particular alkali metal halide-containing, DMC catalysts which result in polyethers with a reduced content of high-molecular impurities. In the present invention, starters containing potassium chloride however prove completely unsuitable, since no catalyst activation was observed.

EP-A 1 577 334 claims starters which are preferably acidified with phosphoric acid in DMC-catalysed alkylene oxide addition processes with continuous starter admetering, which result in increased catalyst life, if relatively short-chain polyethers are to be prepared by means of DMC catalysis, i.e. relatively high starter/alkylene oxide ratios are present during the metering phase. The addition of (acidic) salts is not mentioned. Work carried out in the context of the present invention shows that phosphate-containing starter compounds prevent activation of DMC catalysts.

WO-A 99/14258 likewise claims acidified starters in DMC-catalysed alkylene oxide addition processes with continuous starter admetering. Again, phosphoric acid is emphasised as particularly preferred acid. Salts of sulfuric acid are not mentioned.

U.S. Pat. No. 6,642,423 claims a method for obtaining polyethers with ethylene oxide-containing internal blocks. These can be obtained in one stage directly by DMC-catalysed ethylene oxide addition to low-molecular starter compounds such as glycerol, followed by a propylene oxide block or a block rich in propylene oxide. The method does not utilise the advantageous effect of the presence of a sulfuric acid salt on the suppression of the formation of high-molecular impurities, and is furthermore very expensive, since DMC catalysts in contact with low-molecular starter compounds such as glycerol can be activated only in very high concentrations.

EP-A 1 528 073 claims the two-stage preparation of typical long-chain polyols having an ethylene oxide end block in a reactor. The residual alkalinity resulting from the preceding batch in each case is removed before or during the metering of the starter and the DMC catalyst for the following batch by addition of an acid which forms a salt which is soluble in the long-chain polyol having an ethylene oxide end block. Generally only an alkylbenzenesulfonic acid is suitable for this, since the polyol remnants remaining in the reactor have high equivalent molar masses and are not capable of dissolving salts of purely inorganic acids. What is disadvantageous when using alkylbenzenesulfonic acids are the high costs, which are caused firstly by the high prices of acid, and secondly by the relatively high molar masses of the acids. Furthermore, the claimed process always requires a working-up step such as distillation/filtration or ion exchange, in which the large, conventionally obtained amounts of salt are removed.

WO-A 2006/094979 claims a simplified method for the preparation of DMC catalysts in which the cyanometallate acid is prepared in situ due to the presence of strong mineral acids during the catalyst precipitation. The catalysts thus prepared are conventional DMC catalysts, with which alone no one-pot method without working-up for the preparation of long-chain block copolyethers having internal blocks with block equivalent molar masses of 53 Da to 350 Da can be produced.

In WO-A 01/53381, combinations of Lewis or Brønsted acids and DMC catalysts are used, which are said to result in shortened induction periods upon starting-up the alkylene oxide addition reaction. Synergistic effects on polyether quality which are obtainable by the combination of certain acids/acidic salts with DMC catalysts have not been worked out; rather, the analytical data of the resulting polyether polyols, in particular the elevated contents of primary hydroxyl groups, simply indicate acid-catalysed or DMC-catalysed alkylene oxide addition reactions which take place in parallel.

EP-A 1 073 689 claims the preparation of polyol precursors with hydroxyl values from 100 to 150 mg KOH/g under Lewis-acid conditions, followed by a DMC-catalysed propylene oxide addition step. Separation of the Lewis-acid catalysts, substantially perfluoroalkylsulfonic acid salts of lanthanides, from the precursor before the DMC step does not take place. This is thus a one-pot method without working-up, in which however the striking tendency, described in EP-A 0 855 417, of the Lewis-acid catalysts to form volatile by-products and the high costs thereof have to be classed as disadvantageous.

WO-A 2007/082596 teaches the preparation of DMC catalysts modified with alkali or ammonium salts, which are distinguished by increased activities. It is not possible to carry out a method without working-up departing from low-molecular starter compounds with the method disclosed in WO-A 2007/082596. The positive effects of starters containing sulfuric acid salts with regard to the formation of high-molecular impurities cannot be attained in accordance with the teaching of WO 2007/082596.

SUMMARY OF THE INVENTION

The object was therefore to provide a method without working-up for the preparation of polyether polyols which is distinguished by a low tendency to form high-molecular impurities. The method according to the invention should preferably also be suitable for making polyether polyols having particularly hydrophilic internal blocks accessible. Furthermore, the flexible polyurethane foams which are based on the polyether polyols according to the invention have a higher compressive strength than flexible foams which are based only on filler-free polyether polyols in accordance with the prior art.

Surprisingly, it was discovered that the above object is achieved by a method for the preparation of polyether polyols (1) with a hydroxyl value of 3 mg KOH/g to 150 mg KOH/g, preferably 10 mg KOH/g to 60 mg KOH/mg, particularly preferably 20 mg KOH/g to 50 mg KOH/g, characterised in that
(i) (i-1) an H-functional starter compound A1.1) is reacted with one or more alkylene oxides A1.2) in the presence of a basic catalyst, resulting in an alkoxylate with an equivalent molar mass of 53 Da to 350 Da, and then
(i-2) the component A1) is neutralised with sulfuric acid, the neutralisation of the alkaline, polymerisation-active centres of the crude alkylene oxide addition product being carried out by addition of sulfuric acid such that for from 66 mol % to 100 mol % of the acid used only the first dissociation step becomes effective for neutralisation of the amount of catalyst comprised in the crude polymer, and the separation of the salts formed being dispensed with, resulting in component A), and (ii) then the component A) is reacted with one or more alkylene oxides B1) in the presence of a DMC catalyst B2).

The present invention further provides polyether polyols comprising an acidic sulfuric acid salt, obtainable according to the method of the invention, the use of these polyether polyols for the preparation of polyurethanes, and polyurethanes comprising the polyether polyols according to the invention.

DETAILED DESCRIPTION OF THE INVENTION

In one embodiment of the method according to the invention, acidic sulfuric acid salts A2) are added separately to the polyether polyol A1), and the component A) which is thus obtainable is then reacted further in step ii). A2) is added to A1) in amounts of 95 to 12,000 ppm, preferably in amounts of 95 to 2,400 ppm, and particularly preferably in amounts of 95 to 1,700 ppm, relative to the amount of A1).

The acidic sulfuric acid salts A2) are to be understood to mean hydrogen sulfates A2.1) and sulfates A2.2), the weight ratio of A2.1):A2.2) being 50 to 100:50 to 0.

Hydrogen sulfates A2.1) are
  alkali metal (i.e. Li, Na, K, Rb, Cs) hydrogen sulfates,
  alkaline-earth metal (i.e. Be, Ca, Mg, Sr, Ba) hydrogen sulfates, or
  ammonium hydrogen sulfates of the general formula $[NR^1R^2R^3H]^+[HSO_4]^-$, with
    $R^1R^2R^3$ independently of each other possibly being H, $C_1$-$C_{20}$-alkyl (e.g. methyl, ethyl, propyl, butyl), $C_5$-$C_{20}$-cycloalkyl (e.g. cyclopentyl, cyclohexyl), $C_6$-$C_{20}$ aryl (e.g. phenyl), and the radicals $R^1$, $R^2$ and/or $R^3$ also possibly being linked together such that a cyclic ammonium ion is produced, such as piperazinium, imidazolinium, pyridinium, morpholinium, and sulfates A2.2) are
  alkali metal (i.e. Li, Na, K, Rb, Cs) sulfates,
  alkaline-earth metal (i.e. Be, Ca, Mg, Sr, Ba) sulfates, or
  ammonium sulfates of the general formula $[NR^1R^2R^3H]^+$ $[HSO_4]^-$, with
    $R^1R^2R^3$ independently of each other possibly being H, $C_1$-$C_{20}$-alkyl (e.g. methyl, ethyl, propyl, butyl), $C_5$-$C_{20}$-cycloalkyl (e.g. cyclopentyl, cyclohexyl), $C_6$-$C_{20}$ aryl (e.g. phenyl), and the radicals $R^1$, $R^2$ and/or $R^3$ also possibly being linked together such that a cyclic ammonium ion is produced, such as for example piperazinium, imidazolinium, pyridinium, morpholinium.

Preferably alkali metal hydrogen sulfates, very particularly preferably potassium hydrogen sulfate, are used as hydrogen sulfates A2.1), and alkali metal sulfates and very particularly preferably potassium sulfate as sulfates A2.2) in the method according to the invention.

In a preferred embodiment of the method according to the invention, the component A2) during the procedure is prepared by neutralisation of the polyether polyol A1) with sulfuric acid, forming component A), and is reacted without filtration step directly in step (ii) using DMC catalysis with one or more alkylene oxides B1) to prepare the polyether polyols (1) according to the invention. In this preferred embodiment of the method according to the invention, therefore, component A) is prepared by the steps:

(i-1) reaction of an H-functional starter compound A1.1) with one or more alkylene oxides A1.2) in the presence of a basic catalyst until the component A1) attains equivalent molar masses of 53 Da to 350 Da, and then (i-2) the component A1) is neutralised with sulfuric acid, the neutralisation of the alkaline, polymerisation-active centres of the crude alkylene oxide addition product being carried out by addition of sulfuric acid such that for from 66 mol % to 100 mol % of the acid used only the first dissociation step becomes effective for neutralisation of the amount of catalyst comprised in the crude polymer, and the separation of the salts formed is dispensed with, and (i-3) if necessary the removal of reaction water and traces of water introduced with the acid at an absolute pressure of 1 to 500 mbar and at temperatures of 20 to 200° C., preferably at 80 to 180° C.

The method according to the invention will be described in detail below:

Step (i), Steps (i-1) to (i-3):

(i-1)

The H-functional starter compounds (component A1.1) in one embodiment of the method according to the invention are initially introduced into the reactor in step (i-1) and the basic catalyst is added thereto and the mixture is reacted with one or more alkylene oxides A1.2).

Alkali metal hydroxides, alkali metal and alkaline-earth metal hydrides, alkali metal and alkaline-earth metal carboxylates or alkaline-earth hydroxides may be used as the basic catalyst. Alkali metals are selected from the group consisting of Li, Na, K, Rb, Cs, and the alkaline-earth metals are selected from the group consisting of Be, Ca, Mg, Sr, Ba.

Likewise, organic basic catalysts such as for example amines may be used. These include aliphatic amines or alkanolamines such as N,N-dimethylbenzylamine, dimethylaminoethanol, dimethylaminopropanol, N-methyldiethanolamine, trimethylamine, triethylamine, N,N-dimethylcyclohexylamine, N-methylpyrrolidine, N,N,N',N'-tetramethylethylenediamine, diazabicyclo[2,2,2]octane, 1,4-dimethylpiperazine or N-methylmorpholine. Also aromatic amines such as imidazole and alkyl-substituted imidazole derivatives, N,N-dimethylaniline, 4-(N,N-dimethyl)aminopyridine and partially cross-linked copolymers of 4-vinylpyridine or vinylimidazole and divinylbenzene can likewise be used effectively. A comprehensive overview of suitable amines has been given by M. Ionescu et al. in "Advances in Urethanes Science and Technology", 1998, 14, 151-218. Preferred amine catalysts are tertiary aliphatic amines or alkanolamines and also imidazole and the aforementioned imidazole or pyridine derivatives. Such amine catalysts can be used in concentrations, relative to the amount of product A1) obtained, of 200 ppm to 10,000 ppm; preferably the concentration range is from 200 ppm to 5,000 ppm. Preferred inorganic basic catalysts are the alkali metal hydroxides, potassium hydroxide being very particularly preferred. Such an alkali metal-containing catalyst can be supplied to the H-functional starter compound as an aqueous solution or as a solid. The catalyst concentration relative to the amount of product A1) obtained, in the case of using inorganic basic catalysts, is 40 ppm to 5,000 ppm, preferably 40 ppm to 1,000 ppm, particularly preferably 40 ppm to 700 ppm. The water of solution and/or the water released upon the reaction of the active hydrogen atoms with the catalyst can be removed before the start of metering of one or more alkylene oxides in vacuo at an absolute pressure of 1 to 500 mbar at temperatures of 20 to 200° C., preferably at 80 to 180° C.

Ready-made alkylene oxide addition products of H-functional starter compounds with alkoxylate contents of 0.05 to 50 equivalent %, what are called "polymeric alkoxylates", may also be used as basic catalysts. The alkoxylate content of the catalyst is to be understood to mean the proportion of active hydrogen atoms removed by deprotonation by a base, usually an alkali metal hydroxide, relative to all the active hydrogen atoms which were originally present in the alkylene oxide addition product of the catalyst. The amount of polymeric alkoxylate used will of course depend on the catalyst concentration desired for the amount of product A1), as described in the preceding section.

H-functional starter compounds are those compounds which comprise at least one Zerewitinoff-active hydrogen atom, sometimes also referred to merely as "active hydrogen". A hydrogen bonded to N, O, or S is referred to as Zerewitinoff-active hydrogen if it yields methane by reaction with methylmagnesium iodide in accordance with a method discovered by Zerewitinoff. Typical examples of compounds with Zerewitinoff-active hydrogen are compounds which comprise carboxyl, hydroxyl, amino, imino or thiol groups as functional groups. Suitable H-functional starter compounds mostly have functionalities of from 1 to 35, preferably of from 1 to 8. Their molar masses are from 17 g/mol to 1,200 g/mol. Aminofunctional starters may also be used in addition to the hydroxy-functional starters which are preferably used. Examples of hydroxy-functional starter compounds are methanol, ethanol, 1-propanol, 2-propanol and higher aliphatic mono-ols, in particular fatty alcohols, phenol, alkyl-substituted phenols, propylene glycol, ethylene glycol, diethylene glycol, dipropylene glycol, 1,2-butanediol, 1,3-butanediol, 1,4-butanediol, hexanediol, pentanediol, 3-methyl-1,5-pentanediol, 1,12-dodecanediol, glycerol, trimethylol propane, pentaerythritol, sorbitol, sucrose, hydroquinone, pyrocatechol, resorcinol, bisphenol F, bisphenol A, 1,3,5-trihydroxybenzene, and also condensates of formaldehyde and phenol or urea containing methylol groups. Also highly functional starter compounds based on hydrogenated starch hydrolysis products may be used. Such are described for example in EP-A 1 525 244. Examples of suitable H-functional starter compounds which contain amino groups are ammonia, ethanolamine, diethanolamine, triethanolamine, isopropanolamine, diisopropanolamine, ethylenediamine, hexamethylenediamine, aniline, isomers of toluidine, isomers of diaminotoluene, isomers of diaminodiphenylmethane, and also higher-nuclear products produced upon the condensation of aniline with formaldehyde to give diaminodiphenylmethane, furthermore condensates of formaldehyde and melamine which contain methylol groups, and also Mannich bases. Furthermore also ring-opening products from cyclic carboxylic acid anhydrides and polyols can be used as starter compounds. Examples are ring-opening products from phthalic anhydride, succinic anhydride or maleic anhydride on one hand and ethylene glycol, diethylene glycol, 1,2-butanediol, 1,3-butanediol, 1,4-butanediol, hexanediol, pentanediol, 3-methyl-1,5-pentanediol, 1,12-dodecanediol, glycerol, trimethylol propane, pentaerythritol or sorbitol on the other hand. In addition, it is also possible to use monofunctional or polyfunctional carboxylic acids directly as starter compounds.

Further, also ready-made alkylene oxide addition products of the starter compounds mentioned, i.e. polyether polyols preferably with hydroxyl values of 160 to 1,000 mg KOH/g, preferably 250 to 1,000 mg KOH/g, can be added to the process. Also it is possible to use polyester polyols preferably with hydroxyl values in the range from 6 to 800 mg KOH/g as co-starters with the aim of polyether-ester preparation in the process according to the invention. Polyester polyols suitable for this may for example be prepared from organic dicarboxylic acids with 2 to 12 carbon atoms and polyhydric alcohols, preferably diols, with 2 to 12 carbon atoms, preferably 2 to 6 carbon atoms, according to known methods.

Furthermore, as H-functional starter substances, polycarbonate polyols, polyester carbonate polyols or polyether carbonate polyols, preferably polycarbonate diols, polyester carbonate diols or polyether carbonate diols, preferably in each case with hydroxyl values in the range from 6 to 800 mg KOH/g, can be used as co-starters. These are prepared for example by reaction of phosgene, dimethyl carbonate, diethyl carbonate or diphenyl carbonate with bifunctional or higher-functional alcohols or polyester polyols or polyether polyols.

In the method according to the invention, preferably H-functional starter compounds which are free from amino groups and have hydroxyl groups serve as supports for the active hydrogens such as for example methanol, ethanol, 1-propanol, 2-propanol and higher aliphatic mono-ols, in particular fatty alcohols, phenol, alkyl-substituted phenols, propylene glycol, ethylene glycol, diethylene glycol, dipropylene glycol, 1,2-butanediol, 1,3-butanediol, 1,4-butanediol, hexanediol, pentanediol, 3-methyl-1,5-pentanediol, 1,12-dodecanediol, glycerol, trimethylol propane, pentaerythritol, sorbitol, sucrose, hydroquinone, pyrocatechol, resorcinol, bisphenol F, bisphenol A, 1,3,5-trihydroxybenzene, condensates of formaldehyde and phenol which contain methylol groups, and hydrogenated starch hydrolysis products. Also mixtures of different H-functional starter compounds can be used.

The H-functional starter compounds A1.1) initially introduced into the reactor together with the basic catalyst are reacted in step (i-1) under inert gas atmosphere at temperatures of 80 to 180° C., preferably at 100 to 170° C., with one or more alkylene oxides A1.2), the alkylene oxides in the usual manner being supplied continuously to the reactor such that the safety pressure limits of the reactor system used are not exceeded. In particular in the case of the metering of alkylene oxide mixtures containing ethylene oxide, or pure ethylene oxide, care should be taken that a sufficient inert gas partial pressure is maintained in the reactor during the start-up and metering phase. This can be set for example by noble gases or nitrogen. The reaction temperature can of course be varied within the limits described during the alkylene oxide metering phase: it is advantageous initially to alkoxylate sensitive H-functional starter compounds, such as for example sucrose, at low reaction temperatures, and not to switch to higher reaction temperatures until the starter conversion is adequate. Alkylene oxides can be supplied to the reactor in various ways: metering into the gas phase or directly into the liquid phase is possible, e.g. via a dip pipe or a distributor ring located in the vicinity of the base of the reactor in a thoroughly mixed zone. When metering into the liquid phase, the metering units should be designed to be self-emptying, for example by forming the metering bores on the underside of the distributor ring. Generally, flowing-back of reaction medium into the metering units should be prevented by equipment-related measures, for example by installing non-return valves. If an alkylene oxide mixture is metered, the respective alkylene oxides can be supplied to the reactor separately or as a mixture. Pre-mixing of the alkylene oxides can be achieved for example by a mixing unit located in the common metering section ("inline blending"). It has also proved useful to meter alkylene oxides individually or in a premix on the pump-pressure side into a forced circulation circuit which is guided for example over heat exchangers. It is then advantageous for thorough mixing with the reaction medium to integrate a high-shear mixing unit in the alkylene oxide/reaction medium stream. The temperature of the exothermic alkylene oxide addition reaction is kept at the desired level by cooling. In accordance with the prior art for designing polymerisation reactors for exothermic reactions (e.g. Ullmann's Encyclopedia of Industrial Chemistry, Vol. B4, p. 167 ff., 5th ed., 1992), such cooling generally takes place via the reactor wall (e.g. dual jacket, half-pipe coil) and also by means of further heat-exchange surfaces arranged internally in the reactor and/or externally in the forced circulation circuit, e.g. on cooling coils, cooling cartridges, plate-type heat exchangers, shell-and-tube heat exchangers or mixer heat exchangers. These should be designed such that cooling can be carried out effectively even at the beginning of the metering phase, i.e. with a low filling level.

Generally, thorough mixing of the reactor contents should be ensured in all reaction phases by design and use of commercially available stirring elements, in this case in particular stirrers which are arranged in one stage or in multiple stages or stirrer types which act over a large surface area across the filling height being suitable (see e.g. Handbuch Apparate; Vulkan-Verlag Essen, 1st edition (1990), pp. 188-208). What is of particular relevance, technically speaking, in this case is a mixing energy which is introduced on average across the entire reactor contents, which generally lies in the range from 0.2 to 5 W/l, with correspondingly higher local performance inputs in the region of the stirring elements themselves and if necessary at lower filling levels. In order to attain an optimum stirring action, combinations of flow spoilers (e.g. flat or tubular flow spoilers) and cooling coils (or cooling cartridges) can be arranged in the reactor in accordance with the general prior art, these possibly also extending across the vessel base. The agitator power of the mixing unit can also be varied dependent on filling level during the metering phase, in order to guarantee a particularly high energy input in critical reaction phases. For example, it may be advantageous to mix solids-containing dispersions which may be present at the start of the reaction, for example when using sucrose, particularly thoroughly. Furthermore, in particular when using solid H-functional starter compounds, it should be ensured by the selection of the stirrer unit that sufficient dispersion of the solid in the reaction mixture is guaranteed. Preferably bottom-sweeping stirring stages and also stirring elements which are particularly suitable for suspension are used in this case. Further, the stirrer geometry should contribute to reducing the foaming of reaction products. Foaming of reaction mixtures may for example be observed after the end of the metering and after-reaction phase if residual alkylene oxides are additionally removed in vacuo at absolute pressures in the range from 1 to 500 mbar. Stirring elements which achieve continuous thorough mixing of the liquid surface have proved suitable for such cases. Depending on requirements, the agitator shaft has a base bearing and if necessary further supporting bearings in the vessel. In such case, the agitator shaft can be driven from above or below (with a central or eccentric arrangement of the shaft).

Alternatively, it is also possible to achieve the necessary thorough mixing exclusively via a forced circulation circuit guided via a heat exchanger, or to operate said circuit in addition to the stirrer unit as a further mixing component, the reactor contents being circulated as required (typically 1 to 50 times per hour).

Very widely varying types of reactor are suitable for implementing the method according to the invention. Preferably cylindrical vessels which have a ratio of height to diameter of 1:1 to 10:1 are used. For example spherical, dished, flat or conical bottoms can be used as reactor bottoms.

An after-reaction phase in which residual alkylene oxide reacts off may follow the end of the alkylene oxide metering phase in step (i-1). The end of this after-reaction phase is reached when no further drop in pressure can be detected in the reaction vessel. Traces of unreacted epoxides can be removed after the reaction phase if necessary in vacuo at an absolute pressure of 1 to 500 mbar. The alkaline alkylene oxide addition product can be hydrolysed by water. This hydrolysis step is however not essential for implementing the method according to the invention. The amount of water in this case is up to 15% by weight, relative to the amount of the alkaline alkylene oxide addition product.

(i-2)

The neutralisation of the alkaline, polymerisation-active centres of the crude, if necessary hydrolysed, alkylene oxide addition product A1) from step (i-1) takes place according to the invention in step (i-2) by addition of sulfuric acid such that, for from 66 mol % to 100 mol % of the acid used, only the first dissociation step becomes effective for neutralisation of the amount of catalyst comprised in the crude polymer. This can be achieved for example in that at least 50% more sulfuric acid is used than would be necessary for neutralisation of the basic catalyst. Since the second dissociation step of the sulfuric acid also has a sufficient pKa, for example 0.75 to 1 mol sulfuric acid per mol of catalyst to be neutralised selected from the group sodium hydroxide, potassium hydroxide and/or caesium hydroxide is used in the method according to the invention. The temperature can be varied within wide ranges in the case of hydrolysis and neutralisation; limits can be set in this case by the corrosion resistance of the materials of the neutralisation vessel or by the polyol structure. If groups which are sensitive to hydrolysis, such as for example ester groups, are present in the products, neutralisation can for example be carried out at room temperature. In such cases, it is also recommended to dispense with a preceding, separate hydrolysis step. In accordance with the method according to the invention, the separation of the salts formed is dispensed with.

(i-3)

Once neutralisation has taken place, if necessary in step (i-3) traces of water introduced by the addition of dilute acids, or excess water of hydrolysis can be removed in vacuo at an absolute pressure of 1 to 500 mbar. Anti-ageing agents or antioxidants can be added to the component A) thus obtained if needed during or after the neutralisation. Further working-up steps, such as for example filtration, are not necessary. The component A) has equivalent molar masses of 53 Da to 350 Da.

Step (ii)

The DMC catalyst is added to the component A) obtained from steps (i-1) to (i-3) in one embodiment of the method according to the invention in step (ii) and the mixture is reacted with one or more alkylene oxides B1) until polyether polyols (1) with a hydroxyl value of 3 mg KOH/g to 150 mg KOH/g, preferably of 10 mg KOH/g to 60 mg KOH/g, particularly preferably 20 mg KOH/g to 50 mg KOH/g, are obtained. Furthermore, additionally small amounts (1 to 500 ppm) of other organic or inorganic acids may be added to component A) before the addition of the DMC catalyst, as described for example in WO 99/14258. The reaction of the component A) in step (ii) with one or more alkylene oxides B1) using DMC catalysis can in principle take place in the same reactor as the preparation of component A) in steps (i-1)

to (i-3). The DMC-catalyst concentration, calculated relative to the amount of end product (1), lies in the range from 10 to 1,000 ppm.

DMC catalysts B2) are known in principle from the prior art (see e.g. U.S. Pat. Nos. 3,404,109, 3,829,505, 3,941,849 and U.S. Pat. No. 5,158,922). DMC catalysts which are described e.g. in U.S. Pat. No. 5,470,813, EP-A 700 949, EP-A 743 093, EP-A 761 708, WO 97/40086, WO 98/16310 and WO 00/47649, have very high activity in the polymerisation of epoxides, and permit the preparation of polyether polyols at very low catalyst concentrations (25 ppm or less), so that it is generally no longer necessary to separate the catalyst out from the finished product. Typical examples are the highly active DMC catalysts described in EP-A 700 949, which in addition to a double metal cyanide compound (e.g. zinc hexacyanocobaltate(II)) and an organic complexing ligand (e.g. tert-butanol) also comprise a polyether polyol with a number-average molar mass greater than 500 g/mol.

It is also possible to use the alkaline DMC catalysts disclosed in EP application number 10163170.3.

Cyanide-free metal salts suitable for the preparation of the double metal cyanide compounds preferably have the general formula (I), $$M(X)_n \qquad (I)$$

where
M is selected from the metal cations $Zn^{2+}$, $Fe^{2+}$, $Ni^{2+}$, $Mn^{2+}$, $Co^{2+}$, $Sr^{2+}$, $Sn^{2+}$, $Pb^{2+}$ and $Cu^{2+}$; preferably M is $Zn^{2+}$, $Fe^{2+}$, $Co^{2+}$ or $Ni^{2+}$,
X are one or more (i.e. different) anions, preferably an anion selected from the group of halides (i.e. fluoride, chloride, bromide, iodide), hydroxide, sulfate, carbonate, cyanate, thiocyanate, isocyanate, isothiocyanate, carboxylate, oxalate and nitrate;
n is 1, if X=sulfate, carbonate or oxalate, and
n is 2, if X=halide, hydroxide, cyanate, thiocyanate, isocyanate, isothiocyanate or nitrate,
or suitable cyanide-free metal salts have the general formula (II), $$M_r(X)_3 \qquad (II)$$

where
M is selected from the metal cations $Fe^{3+}$, $Al^{3+}$ and $Cr^{3+}$,
X are one or more (i.e. different) anions, preferably an anion selected from the group of halides (i.e. fluoride, chloride, bromide, iodide), hydroxide, sulfate, carbonate, cyanate, thiocyanate, isocyanate, isothiocyanate, carboxylate, oxalate and nitrate;
r is 2, if X=sulfate, carbonate or oxalate, and
r is 1, if X=halide, hydroxide, cyanate, thiocyanate, isocyanate, isothiocyanate, carboxylate or nitrate,
or suitable cyanide-free metal salts have the general formula (III), $$M(X)_s \qquad (III)$$

where
M is selected from the metal cations $Mo^{4+}$, $V^{4+}$ and $W^{4+}$,
X are one or more (i.e. different) anions, preferably an anion selected from the group of halides (i.e. fluoride, chloride, bromide, iodide), hydroxide, sulfate, carbonate, cyanate, thiocyanate, isocyanate, isothiocyanate, carboxylate, oxalate and nitrate;
s is 2, if X=sulfate, carbonate or oxalate, and
s is 4, if X=halide, hydroxide, cyanate, thiocyanate, isocyanate, isothiocyanate, carboxylate or nitrate, or suitable cyanide-free metal salts have the general formula (IV), $$M(X)_t \qquad (IV)$$

where
M is selected from the metal cations $Mo^{6+}$ and $W^{6+}$,
X are one or more (i.e. different) anions, preferably an anion selected from the group of halides (i.e. fluoride, chloride, bromide, iodide), hydroxide, sulfate, carbonate, cyanate, thiocyanate, isocyanate, isothiocyanate, carboxylate, oxalate and nitrate;
t is 3, if X=sulfate, carbonate or oxalate, and
t is 6, if X=halide, hydroxide, cyanate, thiocyanate, isocyanate, isothiocyanate, carboxylate or nitrate.

Examples of suitable cyanide-free metal salts are zinc chloride, zinc bromide, zinc iodide, zinc acetate, zinc acetylacetonate, zinc benzoate, zinc nitrate, iron(II) sulfate, iron(II) bromide, iron(II) chloride, cobalt(II) chloride, cobalt(II) thiocyanate, nickel(II) chloride and nickel(II) nitrate. Also mixtures of different metal salts can be used.

Metal cyanide salts suitable for the preparation of the double metal cyanide compounds preferably have the general formula (V)

$$(Y)_a M'(CN)_b (A)_c \qquad (V)$$

where
M' is selected from one or more metal cations of the group consisting of Fe(II), Fe(III), Co(II), Co(III), Cr(II), Cr(III), Mn(II), Mn(III), Ir(III), Ni(II), Rh(III), Ru(II), V(IV) and V(V); preferably M' is one or more metal cations of the group consisting of Co(II), Co(III), Fe(II), Fe(III), Cr(III), Ir(III) and Ni(II),
Y is selected from one or more metal cations of the group consisting of alkali metal (i.e. $Li^+$, $Na^+$, $K^+$, $Rb^+$, $Cs^+$) and alkaline-earth metal (i.e. $Be^{2+}$, $Ca^{2+}$, $Mg^{2+}$, $Sr^{2+}$, $Ba^{2+}$),
A is selected from one or more anions of the group consisting of halides (i.e. fluoride, chloride, bromide, iodide), hydroxide, sulfate, carbonate, cyanate, thiocyanate, isocyanate, isothiocyanate, carboxylate, oxalate or nitrate, and
a, b and c are integers, the values for a, b and c being selected such that the metal cyanide salt is electrically neutral; a is preferably 1, 2, 3 or 4; b is preferably 4, 5 or 6; c preferably has the value 0.

Examples of suitable metal cyanide salts are potassium hexacyanocobaltate(III), potassium hexacyanoferrate(II), potassium hexacyanoferrate(III), calcium hexacyanocobaltate(III) and lithium hexacyanocobaltate(III).

Preferred double metal cyanide compounds which are comprised in the DMC catalysts according to the invention are compounds of the general formula (VI)

$$M_x[M'_{x'}(CN)_y]_z \qquad (VI),$$

wherein M is defined as in Formulae (I) to (IV) and
M' is defined as in Formula (V), and
x, x', y and z are integers and selected such that the double metal cyanide compound is electrically neutral.
Preferably
x=3, x'=1, y=6 and z=2,
M=Zn(II), Fe(II), Co(II) or Ni(II) and
M'=Co(III), Fe(III), Cr(III) or Ir(III).

Examples of suitable double metal cyanide compounds are zinc hexacyanocobaltate(III), zinc hexacyanoiridate(III), zinc hexacyanoferrate(III) and cobalt(II) hexacyanocobaltate(III). Further examples of suitable double metal cyanide compounds can be inferred from e.g. U.S. Pat. No. 5,158,922 (column 8, lines 29-66). Zinc hexacyanocobaltate(III) is particularly preferably used.

The organic complexing ligands added during the preparation of the DMC catalysts are disclosed for example in U.S. Pat. No. 5,158,922 (see in particular column 6, lines 9 to 65), U.S. Pat. No. 3,404,109, U.S. Pat. No. 3,829,505, U.S. Pat. No. 3,941,849, EP-A 700 949, EP-A 761 708, JP-A 4145123, U.S. Pat. No. 5,470,813, EP-A 743 093 and WO-A 97/40086). For example, water-soluble organic compounds with heteroatoms, such as oxygen, nitrogen, phosphorus or sulfur, which are capable of forming complexes with the double metal cyanide compound are used as organic complexing ligands. Preferred organic complexing ligands are alcohols, aldehydes, ketones, ethers, esters, amides, ureas, nitriles, sulfides and mixtures thereof. Particularly preferred organic complexing ligands are aliphatic ethers (such as dimethoxyethane), water-soluble aliphatic alcohols (such as ethanol, isopropanol, n-butanol, isobutanol, sec-butanol, tert-butanol, 2-methyl-3-buten-2-ol and 2-methyl-3-butin-2-ol), compounds which comprise both aliphatic or cycloaliphatic ether groups and aliphatic hydroxyl groups (such as ethylene glycol mono-tert-butyl ether, diethylene glycol mono-tert-butyl ether, tripropylene glycol monomethyl ether and 3-methyl-3-oxetanemethanol). Highly preferred organic complexing ligands are selected from one or more compounds of the group consisting of dimethoxyethane, tert-butanol, 2-methyl-3-buten-2-ol, 2-methyl-3-butin-2-ol, ethylene glycol mono-tert-butyl ether and 3-methyl-3-oxetanemethanol.

Optionally, one or more complexing component(s) from the compound classes of polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylic acid-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkylene imines, maleic acid and maleic anhydride copolymers, hydroxyethylcellulose and polyacetals, or of glycidyl ethers, glycosides, carboxylic acid esters of polyhydric alcohols, bile acids or their salts, esters or amides, cyclodextrins, phosphorus compounds, α,β-unsaturated carboxylic acid esters or ionic surface-active or interfacially-active compounds are used in the preparation of the DMC catalysts according to the invention.

Preferably upon the preparation of the DMC catalysts according to the invention, in the first step the aqueous solutions of the metal salt (e.g. zinc chloride), used in a stoichiometric excess (at least 50 mol %) relative to metal cyanide salt, (i.e. at least a molar ratio of cyanide-free metal salt to metal cyanide salt of 2.25 to 1.00) and of the metal cyanide salt (e.g. potassium hexacyanocobaltate) are reacted in the presence of the organic complexing ligand (e.g. tert-butanol) so that a suspension forms which comprises the double metal cyanide compound (e.g. zinc hexacyanocobaltate), water, excess cyanide-free metal salt and the organic complexing ligand. The organic complexing ligand may in this case be present in the aqueous solution of the cyanide-free metal salt and/or of the metal cyanide salt, or it is added directly to the suspension obtained after precipitation of the double metal cyanide compound. It has proved advantageous to mix the aqueous solutions of the cyanide-free metal salt and of the metal cyanide salt and the organic complexing ligand with vigorous stirring. Optionally, the suspension formed in the first step is then treated with a further complexing component. The complexing component in this case is preferably used in a mixture with water and organic complexing ligand. A preferred method of carrying out the first step (i.e. the production of the suspension) takes place using a mixing nozzle, particularly preferably using a jet disperser as described in WO-A 01/39883.

In the second step, the isolation of the solid (i.e. the precursor of the catalyst according to the invention) from the suspension takes place by known techniques, such as centrifugation or filtration.

In a preferred variant embodiment for the preparation of the catalyst, the isolated solid then in a third method step is washed with an aqueous solution of the organic complexing ligand (e.g. by re-suspension and subsequent renewed isolation by filtration or centrifugation). In this manner, for example water-soluble by-products, such as potassium chloride, can be removed from the catalyst according to the invention. Preferably the amount of the organic complexing ligand in the aqueous washing solution is between 40 and 80% by weight, relative to the total solution.

Optionally, in the third step, further complexing component, preferably in the range of between 0.5 and 5% by weight, relative to the total solution, is added to the aqueous washing solution.

Furthermore, it is advantageous to wash the isolated solid more than once. For this, e.g. the first washing operation can be repeated. It is however preferred to use non-aqueous solutions for further washing operations, e.g. a mixture of organic complexing ligand and further complexing component.

The isolated and if necessary washed solid is then, if necessary after grinding, dried at temperatures of generally 20-100° C. and at pressures of generally 0.1 mbar to normal pressure (1013 mbar).

A preferred method of isolating the DMC catalysts according to the invention from the suspension by filtration, filter-cake washing and drying is described in WO-A 01/80994.

The DMC-catalysed reaction step (ii) can generally be carried out according to the same method-related principles as the preparation of component A) in steps (i-1) to (i-3) which took place using base catalysis. Several method-related peculiarities of the DMC-catalysed reaction step (ii) will be discussed below.

In one embodiment, DMC catalyst is added to component A). After heating to temperatures of 60 to 160° C., preferably 100 to 140° C., very particularly preferably 120 to 140° C., the reactor contents in a preferred method variant are stripped with inert gas over a period of preferably 10 to 60 min. with stirring. Upon the stripping with inert gas, volatile constituents are removed with inert gases being introduced into the liquid phase with a simultaneously applied vacuum, at an absolute pressure of 5 to 500 mbar. After metering in typically 5 to 20% by weight alkylene oxide, relative to the amount of component A) initially introduced, the DMC catalyst is activated. The addition of one or more alkylene oxides may take place before, during or after heating of the reactor contents to temperatures of 60 to 160° C., preferably 100 to 140° C., very particularly preferably 120 to 140° C.; it preferably takes place after the stripping. The activation of the catalyst manifests itself by an accelerated drop in the reactor pressure, which indicates the beginning of the alkylene oxide conversion. The desired amount of alkylene oxide or alkylene oxide mixture can then be supplied continuously to the reaction mixture, with a reaction temperature of 20 to 200° C., but preferably of 50 to 160° C., being selected. In many cases, the activation of the catalyst already takes place so quickly that the metering of a separate amount of alkylene oxide for activation of the catalyst can be dispensed with and the continuous metering of an alkylene oxide or several alkylene oxides can be begun directly. Also in the DMC-catalysed reaction step the reaction temperature during the alkylene oxide metering phase can be varied within the limits described. Likewise, one or more alkylene oxides can be supplied to the reactor in the DMC-catalysed reaction step in different ways: metering into the gas phase or directly into the liquid phase is possible, e.g. via a dip pipe or a distributor ring located in the vicinity of the base of the reactor in a thoroughly mixed zone. In the case of DMC-catalysed processes, metering into the liquid phase is the preferred variant.

Once the alkylene oxide metering has ended, an after-reaction phase may follow in which the decrease in the concentration of unreacted alkylene oxide can be quantified by monitoring the pressure. If necessary, the reaction mixture after the end of the after-reaction phase can have small amounts of non-reacted alkylene oxides completely removed, for example in vacuo, at an absolute pressure of 1 to 500 mbar, or by stripping. Volatile constituents, such as for example (residual) alkylene oxides, are removed by stripping, with inert gases or water vapour being introduced into the liquid phase with a vacuum being simultaneously applied (for example by passing inert gas through at an absolute pressure of 5 to 500 mbar). The removal of volatile constituents, such as for example non-reacted alkylene oxides, either in vacuo or by stripping, takes place at temperatures of 20 to 200° C., preferably at 50 to 160° C., and preferably with stirring. Such stripping operations may also be carried out in what are called stripping columns, in which a stream of inert gas or water vapour is guided counter to the product stream. After a constant pressure has been reached or volatile constituents have been removed by vacuum and/or stripping, the product can be discharged from the reactor.

In a further embodiment of the method according to the invention, in step (ii) a starter polyol and DMC catalyst B2) are initially introduced into the reactor system and component A) is supplied continuously together with one or more alkylene oxides B1). Alkylene oxide addition products such as for example polyether polyols, polycarbonate polyols, polyester carbonate polyols, polyether carbonate polyols in each case for example with hydroxyl values in the range from 3 to 1,000 mg KOH/g, preferably from 3 to 300 mg KOH/g, a partial amount of component A), and/or end product (1) according to the invention, which has been prepared separately beforehand, are suitable as starter polyol in step (ii). Preferably a partial amount of component A) or end product (1) according to the invention, which has been prepared separately beforehand, is used as starter polyol in step (ii). Particularly preferably, end product (1) according to the invention, which has been prepared separately beforehand, is used as starter polyol in step (ii).

If the composition of the alkylene oxides is changed once the metering of component A has ended, polyether polyols with multi-block structures can be prepared with this procedure too. It is however also possible to have the metering of component A) and the alkylene oxide metering end simultaneously. Once the reagents have been admetered, an after-reaction phase may follow in which the consumption of alkylene oxide generally can be quantified by monitoring the pressure. Once a constant pressure has been reached, the product can be discharged, if necessary as described above, after applying a vacuum or by stripping in order to remove non-reacted alkylene oxides.

It is also possible in step (ii) to initially introduce the entire amount of component A) and DMC catalyst and to supply one or more H-functional starter compounds, in particular those with equivalent molar masses for example in the range from 9.0 to 350 Da, preferably from 30.0 to 350 Da, continuously together with one or more alkylene oxides B1).

In a further embodiment of the method according to the invention, the reaction product (1) is removed continuously from the reactor. In this procedure, in step (ii) a starter polyol and a partial amount of DMC catalyst B2) are initially introduced into the reactor system and component A) is supplied continuously together with one or more alkylene oxides B1) and DMC catalyst B2), and the reaction product (1) is removed continuously from the reactor. Alkylene oxide addition products such as for example polyether polyols, polycarbonate polyols, polyester carbonate polyols, polyether carbonate polyols, for example with hydroxyl values in the range from 3 to 1000 mg KOH/g, preferably from 3 to 300 mg KOH/g, a partial amount of component A), and/or end product (1) according to the invention, which has been prepared separately beforehand, are suitable as starter polyol in step (ii). Preferably a partial amount of component A) or end product (1) according to the invention, which has been prepared separately beforehand, is used as starter polyol in step (ii). Particularly preferably, end product (1) according to the invention, which has been prepared separately beforehand, is used as starter polyol in step (ii).

In this case, continuous after-reaction steps, for example in a series of reactors or in a tubular reactor, may follow. Volatile constituents can be removed in vacuo and/or by stripping, as described above.

The various method variants for the preparation of polyethers according to the alkylene oxide addition methods with DMC complex catalysis are described for example in WO-A 97/29146 and WO-A 98/03571.

Preferably, the DMC catalyst remains in the end product, but it can also be separated off, for example by treatment with adsorbents. Methods for the separation of DMC catalysts are described for example in U.S. Pat. No. 4,987,271, DE-A 3132258, EP-A 406 440, U.S. Pat. Nos. 5,391,722, 5,099,075, 4,721,818, 4,877,906 and EP-A 385 619.

For the method according to the invention, alkylene oxides (epoxides) with 2 to 24 carbon atoms may be used both for the base-catalysed alkylene oxide addition step (i-1) for obtaining component A1) and for the DMC-catalysed alkylene oxide addition step (ii). The alkylene oxides with 2 to 24 carbon atoms are for example one or more compounds selected from the group consisting of ethylene oxide, propylene oxide, 1-butene oxide, 2,3-butene oxide, 2-methyl-1,2-propene oxide (isobutene oxide), 1-pentene oxide, 2,3-pentene oxide, 2-methyl-1,2-butene oxide, 3-methyl-1,2-butene oxide, 1-hexene oxide, 2,3-hexene oxide, 3,4-hexene oxide, 2-methyl-1,2-pentene oxide, 4-methyl-1,2-pentene oxide, 2-ethyl-1,2-butene oxide, 1-heptene oxide, 1-octene oxide, 1-nonene oxide, 1-decene oxide, 1-undecene oxide, 1-dodecene oxide, 4-methyl-1,2-pentene oxide, butadiene monoxide, isoprene monoxide, cyclopentene oxide, cyclohexene oxide, cycloheptene oxide, cyclooctene oxide, styrene oxide, methylstyrene oxide, pinene oxide, fats epoxidised one or more times as monoglycerides, diglycerides and triglycerides, epoxidised fatty acids, $C_1$-$C_{24}$ esters of epoxidised fatty acids, epichlorohydrin, glycidol, and derivatives of glycidol such as for example methyl glycidyl ether, ethyl glycidyl ether, 2-ethyl hexyl glycidyl ether, allyl glycidyl ether, glycidyl methacrylate and also epoxide-functional alkyloxysilanes such as for example 3-glycidyloxypropyl trimethoxysilane, 3-glycidyloxypropyl triethoxysilane, 3-glycidyloxypropyl tripropoxysilane, 3-glycidyloxypropyl methyldimethoxysilane, 3-glycidyloxypropyl ethyldiethoxysilane, 3-glycidyloxypropyl triisopropoxysilane.

Preferably ethylene oxide and/or propylene oxide, preferably at least 10% ethylene oxide, and very particularly preferably pure ethylene oxide, are used as alkylene oxides A1.2) for the preparation of the polyether polyols A1).

Preferably ethylene oxide and/or propylene oxide are used as alkylene oxides B1) in step (ii).

According to the method of the invention, it is preferred for the composition of the alkylene oxide mixture likewise to be changed upon changing from the base-catalysed alkylene oxide addition step (i-1) to (i-3) to the DMC-catalysed alkylene oxide addition step (ii). If different alkylene oxides are used during the DMC-catalysed alkylene oxide addition step (ii), these may again be admetered either as a mixture or in succession. In the case of the latter metering method, the polyether chains which grow further under DMC catalysis obtain more complicated block structures. In order to obtain defined DMC block structures according to the method of the continuous starter/component A)-admetering method, the continuous starter/component A)-admetering should be terminated jointly with or shortly before the end of the metering of the first alkylene oxide block. Often pure ethylene oxide or mixtures of propylene oxide and ethylene oxide with a high proportion of ethylene oxide are admetered as end block, so that the polyether polyols prepared have 40 to 100% primary OH end groups.

Further monomers which can be copolymerised according to the method of the invention with alkylene oxides using DMC catalysis are for example lactones, lactides, acid anhydrides, cyclic carbonates and carbon dioxide. Their use is described in U.S. Pat. Nos. 3,538,043, 4,500,704, 5,032,671, 6,646,100, EP-A 222 453 and WO-A 2008/013731.

The hydroxyl values of the polyether polyols (1) obtained after the DMC-catalysed alkylene oxide addition step (ii) have values of 3 mg KOH/g to 150 mg KOH/g, preferably 10 to 60 mg KOH/g, particularly preferably 20 to 50 mg KOH/g. Likewise if necessary anti-ageing agents such as antioxidants may be added to the end products.

The polyether polyols (1) may be reacted alone or if necessary in a mixture with further isocyanate-reactive components with organic polyisocyanates, if necessary in the presence of blowing agents, in the presence of catalysts and if necessary with further additives such as foam stabilisers, and thus serve as components of solid or foamed polyurethanes, in particular flexible polyurethane foam such as for example flexible slabstock polyurethane foam and flexible moulded polyurethane foam.

Polyurethanes, preferably solid or foamed polyurethanes, in particular flexible polyurethane foams such as for example flexible slabstock polyurethane foams and flexible moulded polyurethane foams, comprising the polyether polyols (1) according to the invention are likewise provided by the invention.

EXAMPLES

Determination of the Content of High-molecular Impurities

The content of high-molecular impurities was determined following the method described in U.S. Pat. No. 6,013,596.
Hydroxyl Value and Viscosity The hydroxyl values were determined in accordance with the specifications of DIN 53240. The viscosities were determined by means of a rotational viscometer (Physica MCR 51, manufactured by Anton Paar) in accordance with the specifications of DIN 53018.
Molar Mass Distribution The molar mass distribution was determined by means of size exclusion chromatography (SEC). The equipment Agilent 1100 Series from Agilent was used. The polydispersity PD for the molar mass distribution $M_w/M_n$ is given, $M_w$ standing for the weight-average molar mass and $M_n$ for the number-average molar mass. Further particulars:
- column combination: 1 precolumn PSS, 5 µl, 8×50 mm; 2 PSS SVD, 5 µl, 100 Å°, 8×300 mm; 2 PSS SVD, 5 µl, 1000 Å°, 8×300 mm; PSS is the manufacturer of the columns (Polymer Standard Solutions, Mainz)
- evaluation software: WIN GPC from PSS
- solvent: THF (Merck LiChrosolv)
- flow rate: 1 ml/min
- detector type: RI detector (refractive index), Shodex RI 74
- calibration standards used: calibration standard from PSS based on polystyrene.

Raw Materials Used
Catalyst for the Alkylene Oxide Addition (DMC Catalyst):

Double metal cyanide catalyst, comprising zinc hexacyanocobaltate, tert-butanol and polypropylene glycol with a number-average molar mass of 1000 g/mol; described in WO-A 01/80994, Example 6.
Preparation of the Polymeric Alkoxylate I (Basic Catalyst for the Preparation of the Compounds A1))

3677.2 g glycerol and 13.33 g of a 45% by weight solution of KOH in water were placed in a 10 l laboratory autoclave under a nitrogen atmosphere. The autoclave was closed, the stirrer speed was set to 450 rpm, and the mixture was heated to 110° C. The absolute pressure was reduced to 100 mbar, and 2313.7 g propylene oxide was metered into the autoclave over a period of 4.6 h. After an after-reaction time of 180 min. at 110° C., the absolute pressure was reduced again slowly to 100 mbar, and the batch was finally freed from water in vacuo at an absolute pressure of 18 mbar, until an absolute pressure of 10 mbar was obtained at a temperature of 110° C. The alkali number of the polymeric alkoxylate I was 1.0 mg KOH/g, and its KOH content was accordingly 0.1%. Its hydroxyl value was 1121 mg KOH/g. The alkoxylate content was accordingly 0.09%.
Preparation of the Polymeric Alkoxylate II (Basic Catalyst for the Preparation of the Compounds A1))

1278.5 g trimethylol propane and 21.7 g of a 45% by weight solution of KOH in water were placed in a 10 l laboratory autoclave under a nitrogen atmosphere. The autoclave was closed, the stirrer speed was set to 450 rpm and the mixture was heated to 107° C. The absolute pressure was reduced to 100 mbar, and 653.4 g propylene oxide was metered into the autoclave over a period of 3 h. After an after-reaction time of 30 min. at 107° C., the batch was heated thoroughly for 30 min. at an absolute pressure of 10 mbar. After cooling to 25° C., 45.1 g of a 45% by weight solution of KOH in water was added under a nitrogen atmosphere. The mixture was heated to 107° C. and the water was removed in vacuo until an absolute pressure of 10 mbar was reached. Then 4063.6 g propylene oxide was metered in over a period of 8.5 h at 107° C., and after an after-reaction time of 120 min. the mixture was heated thoroughly for 30 min. in vacuo at an absolute pressure of 1 mbar. After cooling to 25° C., 539.4 g of a 45% by weight solution of KOH in water was added under a nitrogen atmosphere. The mixture was heated to 107° C. and the water was removed in vacuo until an absolute pressure of 10 mbar was reached. The alkali number of the polymeric alkoxylate II was 44.1 mg KOH/g, and its KOH content was accordingly 4.41%. The hydroxyl value was 260 mg KOH/g. The alkoxylate content was accordingly 17%.
IRGANOX® 1076

Octadecyl-3-(3,5-di-tert-butyl-4-hydroxyphenyl)propionate. (BASF SE)

Example 1

325.5 g sorbitol and 3.075 g of a 44.82%-strength solution of KOH in water were placed in a 10 l laboratory autoclave under a nitrogen atmosphere. The autoclave was closed and its contents were stripped at 110° C. over a period of 3 h and at a stirrer speed of 450 rpm at an absolute pressure of 100 to 120 mbar by introducing 50 ml nitrogen per minute into the liquid phase via a distributor ring provided with 5 bores and located beneath the liquid level. The mixture was heated to 150° C. with stirring (450 rpm), and 1135.1 g propylene oxide was metered into the autoclave over a period of 3.22 h such that a constant absolute pressure of 5 bar was obtained. After an after-reaction time of 2.45 h, the reactor pressure was set with nitrogen to an absolute pressure of 2.7 bar, and 4540.2 g ethylene oxide was metered in over a period of 9.07 h. During this metering time, the metering was interrupted twice on reaching 5 bar absolute reactor pressure, the mixture was allowed to react away in each case, the pressure was reduced to 2.5 bar (absolute) by letting off the nitrogen, and the alkylene oxide metering was then resumed. Once the ethylene oxide metering had ended, there followed an after-reaction time of 1.5 h. After a thorough heating time of 30 min. at a pressure (absolute) of 10 mbar, the mixture was cooled to 25° C. The catalyst concentration calculated relative to KOH was 230 ppm. 6.475 g of 11.82%-strength sulfuric acid was added to 2006.2 g of the alkaline product (A1-1) at 80° C. and the mixture was agitated for 0.5 h at 80° C. After the addition of 1.028 g IRGANOX® 1076, dewatering was carried out at 110° C. for 3 h at an absolute pressure of 1 mbar. A clear product (A-1) with a viscosity of 730 mPas at 25° C. was obtained.

558.3 g of the polyether polyol A-1) was transferred into a 10 l laboratory autoclave under a nitrogen atmosphere. After the addition of 0.051 g DMC catalyst, the contents of the autoclave were stripped for 30 min. at 130° C. with stirring (gate agitator) at 450 rpm in vacuo at an absolute pressure of 100 to 120 mbar, with 50 ml nitrogen being introduced per minute via a distributor ring located beneath the liquid level. Then, likewise at 130° C. and with stirring at 450 rpm, 441.7 g propylene oxide was metered in over a period of 3.05 h via this distributor ring. The propylene oxide metering started at a pressure (absolute) of 0.05 bar; the absolute maximum pressure attained during the metering phase was 0.8 bar. After an after-reaction time of 0.35 h, the mixture was heated thoroughly for 0.5 h at 130° C. at an absolute pressure of 1 mbar, then cooled to 80° C., and 0.535 g IRGANOX® 1076 was added. The hydroxyl value of the polyether polyol 1 was 57.2 mg KOH/g and the viscosity at 25° C. was 1010 mPas. A polydispersity (Mw/Mn) of 1.10 was determined by means of size exclusion chromatography (polystyrene standards). The contents of high-molecular impurities are listed in Table 1.

Example 2 (Comparison)

The alkaline preliminary product was prepared in a similar manner to Example 1, with merely the catalyst concentration (KOH) being raised from 230 ppm to 1960 ppm. 201.5 g water and 31.52 g 11.95%-strength sulfuric acid were added to 2123 g of the alkaline preliminary product (A1-2) at 80° C. After 0.5 h stirring at 80° C., 0.849 g IRGANOX® 1076 was added, the water was distilled off and the mixture was heated thoroughly for 3 h at 110° C. at an absolute pressure of 1 mbar. After filtration over a depth filter (T 750) at 80° C., a clear intermediate product with a viscosity of 720 mPas at 25° C. was obtained.

561.0 g of the intermediate product was transferred into a 10 l laboratory autoclave under a nitrogen atmosphere. After the addition of 0.054 g DMC catalyst, the contents of the autoclave were stripped for 30 min. at 130° C. with stirring (gate agitator) at 450 rpm at an absolute pressure of 100 to 120 mbar, with 50 ml nitrogen being introduced per minute via a distributor ring located beneath the liquid level. Then, likewise at 130° C. and with stirring at 450 rpm, 440.0 g propylene oxide was metered in over a period of 2.93 h via this distributor ring. The propylene oxide metering started at an absolute pressure of 0.05 bar; the absolute maximum pressure attained during the metering phase was 0.75 bar. After an after-reaction time of 0.33 h, the mixture was heated thoroughly for 0.5 h at 130° C. at a pressure (absolute) of 10 mbar, then cooled to 80° C., and 0.545 g IRGANOX® 1076 was added. The hydroxyl value of the polyether polyol 2 was 58.9 mg KOH/g and the viscosity at 25° C. was 1010 mPas. A polydispersity (Mw/Mn) of 1.18 was determined by means of size exclusion chromatography (polystyrene standards). The contents of high-molecular impurities are listed in Table 1.

TABLE 1

|  | Example 1 | Example 2 (comparison) |
|---|---|---|
| Mol sulfuric acid/mol KOH for neutralising the alkaline preliminary product (A1) | 0.95 | 0.52 |
| Hydroxyl value [mg KOH/g] | 57.2 | 58.9 |
| Viscosity at 25° C. [mPas] | 1010 | 1010 |
| Mw/Mn | 1.10 | 1.18 |
| Contents of high-molecular impurities [ppm]: |  |  |
| 40,000-100,000 Da | 801 | 3790 |
| 100,000-200,000 Da | 0 | 216 |
| >200,000 Da | 0 | 0 |

Example 3

820.7 g glycerol and 1.471 g of a 44.82%-strength solution of KOH in water were placed in a 10 l laboratory autoclave under a nitrogen atmosphere. The autoclave was closed and its contents were stripped at 110° C. over a period of 3 h and at a stirrer speed of 450 rpm (gate agitator) at an absolute pressure of 100 to 120 mbar, with 50 ml nitrogen being introduced per minute via a distributor ring located beneath the liquid level. The mixture was heated to 150° C. with stirring (450 rpm), and the autoclave was supplied with nitrogen up to an absolute pressure of 2.5 bar. Then a mixture of 1289.2 g propylene oxide and 3884.5 g ethylene oxide was metered into the autoclave over a period of 10.53 h such that at most an absolute pressure of 5 bar was obtained. After the alkylene oxide metering had ended, there followed an after-reaction time of 3.25 h. After a thorough heating time of 30 min. at an absolute pressure of 10 mbar, the mixture was cooled to 25° C. The catalyst concentration calculated relative to KOH was 110 ppm. 3.547 g of 11.80%-strength sulfuric acid was added to 2417.1 g of the reaction product A1-3 under a nitrogen atmosphere at 80° C. and the mixture was agitated for 1 h at 80° C. After the addition of 1.210 g IRGANOX® 1076, the product was dewatered for 1 h at an absolute pressure of 18 mbar (water jet vacuum) and then dewatered at 110° C. and a pressure (absolute) of 1 mbar for 3 h. A clear product (A-3) with a viscosity of 231 mPas at 25° C. was obtained.

896.1 g of the product A-3) was transferred into a 10 l laboratory autoclave under a nitrogen atmosphere. After the addition of 0.1054 g phosphoric acid, the mixture was stirred for 20 min. at room temperature. Then 0.185 g DMC catalyst was added and the contents of the autoclave were stripped for 30 min. at 130° C. with stirring at 450 rpm in vacuo at an absolute pressure of 100 to 120 mbar with 50 ml nitrogen being introduced per minute via a distributor ring located beneath the liquid level. Then, likewise at 130° C. and with stirring at 450 rpm, a mixture of 1275.3 g propylene oxide and 3828.1 g ethylene oxide was metered in over a period of 6.02 h via this distributor ring. The propylene oxide metering started at an absolute pressure of 2.5 bar, the absolute maximum pressure attained during the metering phase was 3.94 bar. After an after-reaction time of 0.4 h, the mixture was heated thoroughly for 0.55 h at 130° C. at a pressure (absolute) of 10 mbar, then cooled to 80° C., and 3.008 g IRGANOX® was added. The hydroxyl value of the polyether polyol 3 was 36.5 mg KOH/g and the viscosity at 25° C. was 1380 mPas. A polydispersity (Mw/Mn) of 1.30 was determined by means of size exclusion chromatography (polystyrene standards).

Example 4 (Comparison)

The alkaline preliminary product A1-4 was prepared as in Example 3. 2.5888 g of 10.35%-strength nitric acid was added to 2148.2 g of the alkaline preliminary product A1-4 at 80° C. After 1 h stirring at 80° C., 1.081 g IRGANOX® 1076 was added and the mixture was heated thoroughly for 3 h at 110° C. at a pressure (absolute) of 1 mbar. A clear product A-4 with a viscosity of 229 mPas at 25° C. was obtained.

500 g of the product A-4 was transferred into a 10 l laboratory autoclave under a nitrogen atmosphere. After the addition of 0.093 g phosphoric acid, the mixture was stirred for 20 min at 25° C. Then 0.120 g DMC catalyst was added and the contents of the autoclave were stripped for 30 min. at 130° C. with stirring at 450 rpm at an absolute pressure of 100 to 120 mbar, with 50 ml nitrogen being introduced per minute via a distributor ring located beneath the liquid level. Then, likewise at 130° C. and with stirring at 450 rpm, 1198 g propylene oxide was metered in over a period of 4.33 h via this distributor ring: the propylene oxide metering started at an absolute pressure of 0.05 bar; after initial activation of the DMC catalyst, recognisable by an accelerated pressure drop once the propylene oxide metering had been stopped, the absolute pressure rose continuously during the metering phase, so that the metering had to be interrupted twice and was finally terminated after the above-mentioned 1198 g of metered propylene oxide (70% of the amount of propylene oxide originally intended).

Example 5

466.5 g of the polymeric alkoxylate 1 and 560.4 g glycerol were placed in a 10 l laboratory autoclave under a nitrogen atmosphere. The autoclave was closed and its contents were heated to 150° C. with stirring (gate agitator) at a stirrer speed of 450 rpm. Once this temperature had been reached, the autoclave was supplied with nitrogen up to an absolute pressure of 2.6 bar. Then 5178.3 g ethylene oxide was metered into the autoclave over a period totaling 11.2 h such that at most an absolute pressure of 5 bar was obtained. Owing to the compression of the gas space due to the rising filling level, the ethylene oxide metering had to be interrupted 4 times, the mixture was allowed to react away in each case to a constant pressure level and the absolute pressure was re-set to 2.6 bar before metering the next portion. After the ethylene oxide metering had ended, there followed an after-reaction time of 1.42 h. After a thorough heating time of 30 min. in vacuo, the mixture was cooled to 25° C. The catalyst concentration calculated relative to KOH was 100 ppm. 3.910 g 11.82%-strength sulfuric acid was added to 2938.8 g of the reaction product A1-5 under a nitrogen atmosphere at 80° C. and the mixture was agitated for 1 h at 80° C. After the addition of 1.472 g IRGANOX® 1076, the product was dewatered for 1 h at an absolute pressure of 18 mbar (water jet vacuum) and then heated thoroughly at 110° C. and an absolute pressure of 1 mbar for 3 h. A clear product A-5 with a viscosity of 235 mPas at 25° C. was obtained.

260.4 g of the product A-5 was transferred into a 2 laboratory autoclave under a nitrogen atmosphere. After the addition of 0.061 g DMC catalyst, the contents of the autoclave were stripped for 30 min. at 130° C. with stirring (multi-stage propeller stirrer) at 450 rpm at an absolute pressure of 100 to 120 mbar, with 50 ml nitrogen being introduced per minute via a distributor ring located beneath the liquid level. Then, likewise at 130° C. and with stirring at 450 rpm, 939.6 g propylene oxide was metered in over a period of 4.65 h via this distributor ring. The propylene oxide metering started at an absolute pressure of 0.05 bar; the absolute maximum pressure attained during the metering phase was 1.2 bar. After an after-reaction time of 0.33 h, the mixture was heated thoroughly for 0.5 h at 130° C. at a pressure (absolute) of 10 mbar, then cooled to 80° C., and 0.628 g IRGANOX® 1076 was added. The hydroxyl value of the polyether polyol 5 was 53.4 mg KOH/g and the viscosity at 25° C. was 602 mPas. A polydispersity (Mw/Mn) of 1.03 was determined by means of size exclusion chromatography (polystyrene standards). The contents of high-molecular impurities are listed in Table 2.

Example 6 (Comparison)

The alkaline preliminary product A1-6 was prepared as in Example 5. 2.5376 g of 20.35%-strength perchloric acid was added to 2869.1 g of the alkaline product A1-6 at 80° C. After 1 h stirring at 80° C., the product was dewatered for 1 h at a pressure (absolute) of 18 mbar (water jet vacuum) and then, after the addition of 1.455 g IRGANOX® 1076, heated thoroughly at 110° C. and at a pressure (absolute) of 1 mbar over a period of 3 h. A clear product A-6 with a viscosity of 236 mPas at 25° C. was obtained.

259.6 g of the product A-6 was transferred into a 2 l laboratory autoclave under a nitrogen atmosphere. After the addition of 0.060 g DMC catalyst, the contents of the autoclave were stripped for 30 min. at 130° C. with stirring (multi-stage propeller stirrer) at 450 rpm at an absolute pressure of 100 to 120 mbar, with 50 ml nitrogen/min. being introduced via a distributor ring located beneath the liquid level. Then, likewise at 130° C. and with stirring at 450 rpm, 940.4 g propylene oxide was metered in over a period of 4.65 h via this distributor ring. The propylene oxide metering started at an absolute pressure of 0.05 bar, the absolute maximum pressure attained during the metering phase was 1.3 bar. After an after-reaction time of 0.97 h, the mixture was heated thoroughly for 0.5 h at 130° C. at a pressure (absolute) of 10 mbar, then cooled to 80° C., and 0.657 g IRGANOX® 1076 was added. The hydroxyl value of the polyether polyol 6 was 53.6 mg KOH/g and the viscosity at 25° C. was 613 mPas. A polydispersity (Mw/Mn) of 1.05 was determined by means of size exclusion chromatography (polystyrene standards). The contents of high-molecular impurities are listed in Table 2.

TABLE 2

| | Example 5 | Example 6 (comparison) |
|---|---|---|
| Neutralising acid (mol acid/mol KOH for | Sulfuric acid (0.9) | Perchloric acid (1.0) |

TABLE 2-continued

|  | Example 5 | Example 6 (comparison) |
|---|---|---|
| neutralising the alkaline preliminary product A1) |  |  |
| Hydroxyl value [mg KOH/g] | 53.4 | 53.6 |
| Viscosity at 25° C. [mPas] | 602 | 613 |
| Mw/Mn | 1.03 | 1.05 |
| Contests of high-molecular impurities [ppm]: |  |  |
| 40,000-100,000 Da | 656 | 945 |
| 100,000-200,000 Da | 0 | 260 |
| >200,000 Da | 0 | 0 |

Example 7

13.56 g of the polymeric alkoxylate II and 1215.2 g trimethylol propane were placed in a 10 l laboratory autoclave under a nitrogen atmosphere. The autoclave was closed and its contents were melted by heating to 80° C. Residual oxygen was removed, once the filling nozzle had been closed, at 25° C. by pressurising three times with nitrogen to an absolute pressure of 3 bar and subsequent releasing of the excess pressure down to atmospheric pressure. Then the mixture was heated to 150° C. with stirring (gate agitator) at a stirrer speed of 450 rpm. Once this temperature had been reached, the autoclave was supplied with nitrogen up to an absolute pressure of 2.4 bar. Then 4771.5 g ethylene oxide was metered into the autoclave over a period totaling 8.41 h such that at most an absolute pressure of 4.8 bar was obtained. Owing to the compression of the gas space due to the rising filling level, the ethylene oxide metering had to be interrupted 3 times, the mixture was allowed to react away in each case to a constant pressure level and the absolute pressure was re-set to 2.4 bar before the next portion was metered. After the ethylene oxide metering had ended, there followed an after-reaction time of 50 min. After a thorough heating time of 30 min. at an absolute pressure of 10 mbar, the mixture was cooled to 25° C. The catalyst concentration calculated relative to KOH was 100 ppm. 3.690 g 11.887%-strength sulfuric acid was added to 2783.0 g of the reaction product A1-7 under a nitrogen atmosphere at 80° C. and the mixture was agitated for 1 h at 80° C. Then the product was dewatered for 1 h at a pressure (absolute) of 18 mbar (water jet vacuum) and then heated thoroughly at 110° C. and a pressure (absolute) of 1 mbar for 3 h. After the addition of 1.401 g IRGANOX® 1076, a clear product A-7 with a viscosity of 269 mPas at 25° C. was obtained.

100 g of the product A-7 was transferred into a 1 l high-grade steel pressure reactor under a nitrogen atmosphere. After the addition of 0.014 g DMC catalyst, the mixture was heated to 130° C. and stripped for 30 min. at an absolute pressure of 0.1 bar with stirring and 50 ml nitrogen per minute being passed through. Then the metering of 364 g propylene oxide was started at an absolute reactor pressure of 0.1 bar, the DMC catalyst being active directly at the start of metering. The metering time was 30 min., during which the absolute reactor pressure rose to 2.8 bar. After an after-reaction time of 30 min. at 130° C., readily volatile contents were distilled off at 90° C. over a period of 30 min. at an absolute pressure of 10 mbar and the reaction mixture was then cooled to 25° C.

The hydroxyl value of the polyether polyol 7 was 52.4 mg KOH/g at a viscosity (25° C.) of 701 mPas.

Example 8 (Comparison)

The alkaline preliminary product A1-8 was prepared as in Example 7. 0.2055 g of 85%-strength phosphoric acid was added to 987.1 g of the alkaline preliminary product A1-8 at 80° C. Then the product was dewatered for 1 h at an absolute pressure of 18 mbar (water jet vacuum) and then heated thoroughly at 110° C. and an absolute pressure of 1 mbar for 3 h. After the addition of 0.495 g IRGANOX® 1076, a clear product A-8 with a viscosity of 268 mPas at 25° C. was obtained.

100 g of the product A-8 was transferred into a 1 l high-grade steel pressure reactor under a nitrogen atmosphere. After the addition of 0.014 g DMC catalyst, the mixture was heated to 130° C. and stripped for 30 min. at an absolute pressure of 0.1 bar with stirring and 50 ml nitrogen per minute being passed through. Then the metering of propylene oxide was started at an absolute reactor pressure of 0.1 bar. A total of 75 g propylene oxide was metered in at 130° C. within 6 min., without activation of the catalyst being observed. The absolute pressure in the reactor rose to 5.8 bar during the propylene oxide metering. Once the propylene oxide metering had been stopped, no activation of the catalyst occurred within 30 min.

Example 9

1049.0 g propylene glycol and 2.748 g of a 44.63%-strength solution of KOH in water were placed in a 10 l laboratory autoclave under a nitrogen atmosphere. Residual oxygen was removed, once the filling nozzle had been closed, at 25° C. by pressurising four times with nitrogen to an absolute pressure of 3 bar and subsequent releasing of the excess pressure down to atmospheric pressure. The mixture was heated to 150° C. with stirring (multi-stage propeller stirrer at 450 rpm), and 3963.0 g propylene oxide was metered into the autoclave over a period of 14 h. After the alkylene oxide metering had ended, there followed an after-reaction time of 6 h. After a thorough heating time of 30 min. at 150° C. and at an absolute pressure of 10 mbar, the mixture was cooled to 80° C. The catalyst concentration calculated relative to KOH was 245 ppm. 17.862 g 12.01%-strength sulfuric acid was added to the reaction product A1-9 under a nitrogen atmosphere at 80° C. and the mixture was agitated for 1 h at 80° C. After the addition of 3.015 g IRGANOX® 1076, the product was dewatered for 1 h at an absolute pressure of 18 mbar (water jet vacuum) and then at 110° C. and an absolute pressure of 1 mbar for 3 h. The product A-9 obtained had a viscosity of 57 mPas at 25° C. and a hydroxyl value of 309 mg KOH/g.

217.9 g of the product A-9 was transferred into a 2 l laboratory autoclave under a nitrogen atmosphere. After the addition of 0.041 g DMC catalyst, the contents of the autoclave were stripped for 30 min. at 130° C. with stirring (propeller stirrer) at 450 rpm at an absolute pressure of 100 to 120 mbar, with 50 ml nitrogen being introduced per minute via a distributor ring located beneath the liquid level. Then, likewise at 130° C. and with stirring at 450 rpm, 41.1 g propylene oxide was metered in over a period of 0.42 h via this distributor ring; the metering began at an absolute pressure of 0.05 bar. After an after-reaction time of 30 min., the reactor was supplied with nitrogen up to an absolute pressure of 2.5 bar. Then 342.9 g ethylene oxide was metered in over a period of 1.18 h. In this case, the procedure was such that at most an absolute pressure of 5 bar was obtained. After an after-reaction time of 0.25 h, a further 418.3 g propylene oxide was metered in over a period of 3.85 h. There followed an after-reaction time of 0.95 h, the product was thereupon heated thoroughly for 0.5 h at 130° C. in vacuo at an absolute pressure of 10 mbar, then cooled to 80° C., and 0.616 g IRGANOX® 1076 was added. The hydroxyl value of the polyether polyol 9 was 66.1 mg KOH/g. A polydispersity (Mw/Mn) of 1.22 was determined by means of size exclusion chromatography (polystyrene standards).

Example 10

244.3 g propylene glycol and 0.595 g imidazole were placed in a 2 l laboratory autoclave under a nitrogen atmosphere. Residual oxygen was removed, once the filling nozzle had been closed, at 25° C. by pressurising four times with nitrogen to an absolute pressure of 3 bar and subsequent releasing of the excess pressure down to atmospheric pressure. The mixture was heated to 105° C. with stirring (anchor-type stirrer at 800 rpm), and 901.3 g ethylene oxide was metered into the autoclave over a period of 6 h. After the ethylene oxide metering had ended, there followed an after-reaction time of 0.72 h. After a thorough heating time of 30 min. at 105° C. at an absolute pressure of 10 mbar, the mixture was cooled to 80° C. The catalyst concentration was 519 ppm. 7.153 g 12.01%-strength sulfuric acid was added to the reaction product A1-10 under a nitrogen atmosphere at 80° C. and the mixture was agitated for 0.5 h at 80° C. After the addition of 0.625 g IRGANOX® 1076, the product was dewatered for 1 h at an absolute pressure of 18 mbar (water jet vacuum) and then dewatered at 110° C. and at an absolute pressure of 1 mbar for 3 h. The product A-10 obtained had a viscosity of 68 mPas at 25° C. and a hydroxyl value of 333 mg KOH/g.

101.1 g of the product A-10 was transferred into a 2 l laboratory autoclave under a nitrogen atmosphere. After the addition of 0.243 g DMC catalyst, the contents of the autoclave were stripped for 30 min. at 130° C. with stirring (propeller stirrer) at 450 rpm at an absolute pressure of 100 to 120 mbar, with 50 ml nitrogen being introduced per minute via a distributor ring located beneath the liquid level. Then, likewise at 130° C. and with stirring at 800 rpm, 1099.8 g propylene oxide was metered in over a period of 7.22 h via this distributor ring; the metering began at an absolute pressure of 0.05 bar. After an after-reaction time of 30 min, the product was heated thoroughly for 30 min. at 130° C. at an absolute pressure of 10 mbar, then cooled to 80° C., and 0.631 g IRGANOX® 1076 was added. The hydroxyl value of the polyether polyol 10 was 29.2 mg KOH/g. A polydispersity (Mw/Mn) of 1.19 was determined by means of size exclusion chromatography (polystyrene standards).

Production of Flexible Slabstock Polyurethane Foams with Polyether Polyols Prepared According to Example 1 (Inventive) and Example 2 (Comparison)

Further raw materials used:

Arcol® 1108: polyether polyol with a hydroxyl value of 48 mg KOH/g, prepared by a fully continuous DMC-catalysed alkylene oxide addition process, with a mixture of propylene oxide and ethylene oxide in a weight ratio of 89.2/10.8 being attached to a mixture of starter compounds (glycerol and propylene glycol in a weight ratio of 83.5/16.5).

Tegostab® B2370: polyether siloxane-based foam stabiliser (Evonik Goldschmidt GmbH, Germany).

Addocat® 108: mixture of amine-type catalysts for the production of flexible polyurethane foam Dabco® T-9 Catalyst: tin(II) salt of 2-ethylhexanoic acid T80: mixture of 2,4- and 2,6-TDI in a weight ratio of 80:20 and with an NCO content of 48% by weight.

T65: mixture of 2,4- and 2,6-TDI in a weight ratio of 65:35 and with an NCO content of 48% by weight.

Under the processing conditions conventional for the production of flexible slabstock polyurethane foams, the starting components were processed in a one-stage method by means of slabstock foaming. The characteristic of the processing was 108 in all cases. The characteristic indicates the proportion of isocyanate groups in the polyisocyanates to the hydrocarbons in the polyol formulation which are reactive with respect to the isocyanates. The characteristic 108 corresponds to a ratio of isocyanate groups to the hydrocarbons which are reactive with respect to isocyanates of 1.08:

characteristic=[(amount of isocyanate used):(amount of isocyanate calculated)]·100

The density was determined in accordance with DIN EN ISO 845.

The compressive strength (CLD 40%) was determined in accordance with DIN EN ISO 3386-1-98 at a deformation of 40%, 4th cycle.

The tensile strength was determined in accordance with DIN EN ISO 1798.

The compression set (DVR 90%) was determined in accordance with DIN EN ISO 1856-2000 at 90% deformation.

TABLE 3

Flexible slabstock polyurethane foams; formulations and properties

| | | Example | |
|---|---|---|---|
| | | 11 | 12 (comparison) |
| Polyol ether polyol 1 (from Example 1) | | 50 | — |
| Polyol ether polyol 2 (from Example 2) | | — | 50 |
| Arcol ® 1108 | | 50 | 50 |
| Water | | 3.50 | 3.50 |
| Tegostab ® B 2370 | | 1.20 | 1.20 |
| Addocat ® 108 | | 0.10 | 0.10 |
| Dabco ® T9 Catalyst | | 0.16 | 0.16 |
| T80 | | 22.61 | 22.69 |
| T65 | | 22.61 | 22.69 |
| Cell structure | | fine | fine |
| Density | [kg/m³] | 30.0 | 30.9 |
| Tensile strength | [kPa] | 74 | 75 |
| Compressive strength | [kPa] | 5.5 | 4.6 |
| DVR 90% | [%] | 5.6 | 5.6 |

The results listed in Table 3 show that a flexible foam produced with a mixture of polyether polyols comprising a polyether polyol manufactured according to the method of the invention has a significantly higher compressive strength (Example 11) than a flexible foam which was produced exclusively on the basis of polyether polyols not in accordance with the invention (comparison example 12).

What is claimed is:

1. A method for the preparation of polyether polyols (1) with a hydroxyl value of 3 mg KOH/g to 150 mg KOH/g, comprising
   (i) preparing a component A) by
     (i-1) forming a crude alkoxylate with an equivalent molar mass of 53Da to 350 Da by reacting a first H-functional starter compound A1.1) with one or more alkylene oxides A1.2) in the presence of a basic catalyst, and then
     (i-2) neutralizing said crude alkoxylate with sulfuric acid, wherein the neutralisation of the alkaline, polymerisation-active centres of said crude alkoxylate is carried out by addition of sulfuric acid such that for from 66 mol % to 100 mol % of the acid used, only the first dissociation step of sulfuric acid is effective for neutralisation of the amount of catalyst present in the crude alkoxylate, and the separation of the salts formed being dispensed with, and (ii) reacting said component A) with one or more alkylene oxides B1) in the presence of a DMC catalyst B2).

2. The method according to claim 1, wherein after step (i-2) in step (i-3) the removal of reaction water and traces of water introduced with the acid takes place at an absolute pressure of 1 to 500 mbar and at temperatures of 20 to 200° C.

3. The method according to claim 1, wherein said basic catalyst comprises at least one compound selected from the group consisting of alkali metal hydroxides, alkaline-earth metal hydroxides, alkali metal hydrides, alkaline-earth metal hydrides, alkali metal carboxylates and alkaline-earth metal carboxylates.

4. The method according to claim 1, wherein said basic catalyst comprises an alkali metal hydroxide.

5. The method according to claim 1, wherein said basic catalyst is selected from the group consisting of sodium hydroxide, potassium hydroxide, caesium hydroxide and mixtures thereof.

6. The method according to claim 1, wherein the concentration of basic catalyst is 40 ppm to 5,000 ppm, relative to the resulting amount of crude alkoxylate product.

7. The method according to claim 1, characterised in that at least one amine is used as basic catalyst.

8. The method according to claim 1, wherein in step (ii) a second H-functional starter compound and DMC catalyst B2) are initially introduced into the reactor system, and component A) is supplied continuously together with one or more alkylene oxides B1).

9. The method according to claim 8, wherein in step (ii) said second H-functional starter compound comprises a polyether polyol end product (1) according to the invention, which has been prepared separately beforehand.

10. The method according to claim 8, wherein in step (ii) said second H-functional starter compound comprises component A).

11. The method according to claim 1, wherein in step (ii) the entire amount of component A) and DMC catalyst B2) are initially introduced and one or more third H-functional starter compounds are supplied continuously together with one or more alkylene oxides B1).

12. The method according to claim 1, wherein in step (ii) a second H-functional starter compound and a DMC catalyst B2) are initially introduced into the reactor system, and component A) is supplied jointly continuously with one or more alkylene oxides B1) and DMC catalyst B2), and the resultant polyether polyol (1) is removed continuously from the reactor system as reaction product.

13. The method according to claim 12, wherein in step (ii) said second H-functional starter compound comprises polyether polyol end product (1) according to the invention, which has been prepared separately beforehand.

14. The method according to claim 12 wherein in step (ii) said second H-functional starter compound comprises component A).

15. The method according to claim 1, wherein said one or more alkylene oxides A1.2) to be metered in step (i-1) comprise at least 10% by weight ethylene oxide, based on 100% by weight of said alkylene oxides.

16. The method according to claim 1, wherein component A) is split into two portions, and in step (ii) a second H-functional starter compound and DMC catalyst B2) are initially introduced into the reactor system, with said second H-functional starter compound comprising a first portion of component A) and the second portion of component A) is supplied continuously together with one or more alkylene oxides B1).

17. The method according to claim 1, wherein component A) is split into two portions, in step (ii) a second H-functional starter compound and DMC catalyst B2) are initially introduced into the reactor system, with said second H-functional starter compound comprising a first portion of component A), and the second portion of component A) is supplied jointly continuously with one or more alkylene oxides B1) and DMC catalyst B2), and the resultant polyether polyol (1) is removed continuously from the reactor system as reaction product.

18. Polyether polyols produced by the process of claim 1.

19. A polyurethane comprising the reaction product of one or more polyether polyols according to claim 18 with at least one polyisocyanate component.

* * * * *